United States Patent
Ye

(10) Patent No.: US 10,702,531 B2
(45) Date of Patent: Jul. 7, 2020

(54) PYRAZOLOPYRIMIDINE COMPOUND AS PI3K INHIBITOR AND USE THEREOF

(71) Applicant: Shenzhen Bo Li Jian Medicine Co., Ltd., Shenzhen, Guangdong (CN)

(72) Inventor: Baohuan Ye, Guangdong (CN)

(73) Assignee: Shenzhen Bo Li Jian Medicine Co., Ltd., Shenzhen (CN)

( * ) Notice: Subject to any disclaimer, the term of this patent is extended or adjusted under 35 U.S.C. 154(b) by 0 days.

(21) Appl. No.: 16/398,322

(22) Filed: Apr. 30, 2019

(65) Prior Publication Data

US 2019/0255057 A1 Aug. 22, 2019

Related U.S. Application Data

(63) Continuation of application No. PCT/CN2017/106694, filed on Oct. 18, 2017.

(30) Foreign Application Priority Data

Nov. 2, 2016 (CN) .......................... 2016 1 0945311
Oct. 13, 2017 (CN) .......................... 2017 1 0954238

(51) Int. Cl.
*C07D 487/04* (2006.01)
*A61K 31/519* (2006.01)
*A61P 37/02* (2006.01)
*A61P 35/00* (2006.01)
*A61K 45/06* (2006.01)
*A61P 35/02* (2006.01)

(52) U.S. Cl.
CPC ............ *A61K 31/519* (2013.01); *A61K 45/06* (2013.01); *A61P 35/00* (2018.01); *A61P 35/02* (2018.01); *A61P 37/02* (2018.01); *C07D 487/04* (2013.01)

(58) Field of Classification Search
CPC .................................................. C07D 487/04
See application file for complete search history.

(56) References Cited

U.S. PATENT DOCUMENTS

2012/0157430 A1 6/2012 Li et al.
2014/0371246 A1 12/2014 Evarts et al.

FOREIGN PATENT DOCUMENTS

| WO | 0123387 A2 | 4/2001 |
| WO | 2004022561 A1 | 3/2004 |
| WO | 2007044401 A2 | 4/2007 |
| WO | 2012087784 A1 | 6/2012 |

OTHER PUBLICATIONS

Vanhaesebroeck, B. et al., The emerging mechanisms of isoform-specific PI3K signalling, Nature Reviews Molecular Cell Biology, May 2010, pp. 329-341, vol. 11.
Vivanco, L and Sawyers, C. L., The phosphatidylinositol 3-kinase-akt pathway in human cancer, Nature Reviews Cancer, Jul. 2002, pp. 489-501, vol. 2.
Furman, R. R. et al., Idelalisib and Rituximab in Relapsed Chronic Lymphocytic Leukemia, The New England Journal of Medicine, Mar. 13, 2014, pp. 997-1007, vol. 370, No. 11.
O'Brien, S. et al., A phase 2 study of idelalisib plus rituximab in treatment-naïve older patients with chronic lymphocytic leukemia, Blood, Dec. 17, 2015, pp. 2686-2694, vol. 126, No. 25.
Ali, K. et al., Inactivation of the PI3K p110δ breaks regulatory T cell-mediated immune tolerance to cancer, Nature, Jun. 19, 2014, pp. 407-411, vol. 510, No. 7505.
Puri, K. D. et al., IC87114, a Selective Inhibitor of PI3Kδ Suppresses Joint Inflammation and Bone Erosion in collagen-Induced Arthritis in Rat (50.14), J. Immunol., Apr. 1, 2009, vol. 182, Issue 1 Supplement.
Maxwell, M. J. et al., Attenuation of phosphoinositide 3-kinase δ signaling restrains autoimmune disease, Journal of Autoimmunity, 2012, pp. 381-391, vol. 38.
Suárez-Fueyo, A. et al., Enhanced Phosphoinositide 3-Kinase δ Activity Is a Frequent Event in Systemic Lupus Erythematosus That Confers Resistance to Activation-Induced T Cell Death, Journal of Immunology, 2011, pp. 2376-2385, vol. 187.
Examination Report of counterpart Indian Patent Application No. 201927017187 dated Feb. 5, 2020.

*Primary Examiner* — Emily A Bernhardt

(57) ABSTRACT

The present application relates to a pyrazolopyrimidine compound of Formula (I) and a pharmaceutically acceptable salt thereof. Such compounds can be used to inhibit the activity of a lipid kinase PI3K, and can also be used to treat diseases mediated by PI3K, such as cancers, inflammatory diseases, and autoimmune diseases. The present application also relates to a pharmaceutical composition containing such compounds, a method for preparing such compounds, and use of such compounds or pharmaceutical compositions in the preparation of a drug for treating cancers, inflammatory diseases, and autoimmune diseases mediated by PI3K.

1 Claim, No Drawings

PYRAZOLOPYRIMIDINE COMPOUND AS PI3K INHIBITOR AND USE THEREOF

CROSS-REFERENCE OF RELATED APPLICATIONS

The present application is a Continuation Application of PCT patent application no. PCT/CN2017/106694 filed on Oct. 18, 2017, which claims the priorities of Chinese patent application nos. 201610945311.4 filed on Nov. 2, 2016 and 201710954238.1 filed on Oct. 13, 2017. All the above are hereby incorporated by reference.

FIELD OF TECHNOLOGY

The present application belongs to the field of pharmaceutical chemistry, and particularly relates to a class of PI3K inhibitors, pharmaceutical compositions thereof, preparation method thereof, and use thereof.

BACKGROUND TECHNOLOGY

Phosphoinositide 3-kinases (PI3Ks) are ubiquitous lipid kinases, functioning not only as a signal transducer downstream of a receptor at a cell surface but also as a signal transducer in constituent intracellular membrane and protein trafficking pathways (Vanhaesebroeck, B. et al., Nature Rev. Mol. Cell Biol., 2010, 11, 329-341). The PI3K family of lipid kinases can be divided, based on their physiological substrate specificity, into three classes: Class I, Class II, and Class III. Among these three classes, Class I has been widely studied. Class I PI3Ks are heterodimers composed of a p110 catalytic subunit and a regulatory subunit. Class I PI3Ks are further divided into Class Ia kinases and Class Ib kinases. Class Ia kinases are composed of three different catalytic subunits (p110α, p110β and p110δ), which dimerize with five different regulatory subunits (p85α, p55α, p50α, p85β, and p55γ), wherein all the catalytic subunits can interact with all the regulatory subunits to form various heterodimers, which are called PI3Kα, PI3Kβ, and PI3Kδ. p110α and p110β are expressed essentially in all cell types, while p110δ is expressed primarily in leukocytes. The single-type Class Ib kinases are composed of p110γ catalytic subunits interacting with p101 regulatory subunits, and are called PI3Kγ. Like p110δ, Class Ib kinases are expressed primarily in leukocytes.

PI3Ks play a role in tumorigenesis in many kinds of cancers, due to the dysregulation or overactivation of PI3K/AKT pathway (Vivanco and Sawyers, Nature Rev. Cancer, 2002, 2, 489-501). Among the four isoforms, PI3Kδ plays a role in controlling the survival of B-cells in certain B-cell cancers. For example, PI3Kδ is important to the survival of non-Hodgkin's lymphoma (NHL) and chronic lymphocytic leukemia (CLL). It has been clinically proven that PI3Kδ inhibitor, idelalisib, is capable of treating CLL (Furman, R. R., et al., The New Englang Journal of Medicine, 2014, 370, 997-1007; O'Brien, S., et al., Blood, 2015, 126, 2686-2694), and thus it has been approved by the US FDA for treatment of these diseases. This adequately shows that B-cell lymphoma and leukemia including NHL and CLL can be treated by inhibiting the activity of PI3Kδ.

In addition, inhibition of PI3Kδ can break regulatory T-cell-mediated immune tolerance to tumors, and increase immune responses, thus leading to regression of a tumor in an animal model (Ali, K. et al., Nature, 2014, 510, 407-411). These findings show that inhibition of PI3Kδ is valuable to the treatment of tumors, especially those with insufficient immune response, such as, breast cancers, lung cancers (including small cell lung cancer, non-small cell lung cancer, and bronchioloalveolar carcinoma), prostate cancers, cholangiocarcinoma, bone cancers, bladder cancers, head and neck cancers, renal cancers, liver cancers, gastrointestinal tissue cancers, esophageal cancers, ovarian cancers, pancreatic cancers, skin cancers, testicular cancers, thyroid cancers, uterine cancer, cervical cancers, vaginal cancers, leukemia, multiple myeloma, lymphoma, etc.

In addition to tumors, evidence also show that PI3Kδ also plays an important role in inflammations and autoimmune diseases (Puri, K. D. et al., J. Immunol., 2009, 182 (Suppl. 50), 14; Maxwell, M. J. et al., J. Autoimmunity, 2012, 38, 381-391; Suarez-Fueyo, A. et al., J. Immunol., 2011, 187, 2376-2385). Thus, inhibition of PI3Kδ can be used for treatment of inflammatory diseases and autoimmune diseases, including but not limited to, dermatitis, rheumatoid arthritis, allergic rhinitis, asthma, Crohn's disease, chronic obstructive pulmonary disease (COPD), systemic lupus erythematosus, psoriasis, multiple sclerosis, activated PI3Kδ syndrome, Sjogren syndrome, etc.

The present application relates to a new generation of PI3K inhibitor which can be used in treatment of cancers, inflammatory diseases, and autoimmune diseases.

SUMMARY

The present application, in one aspect, provides a compound of Formula (I):

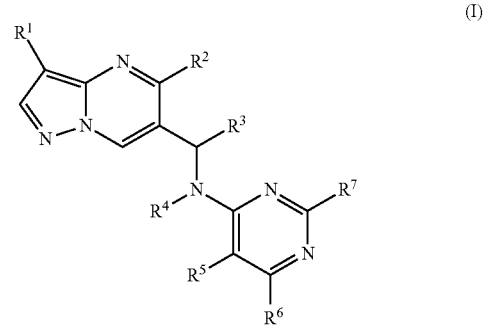

or a pharmaceutical salt thereof, wherein:

$R^1$ is selected from a group consisting of H, halogen, cyano, alkyl, alkenyl, alkynyl, aryl, heteroaryl, cycloalkyl, and heterocycloalkyl, wherein said alkyl, alkenyl, alkynyl, aryl, heteroaryl, cycloalkyl, or heterocycloalkyl may be optionally substituted with one to five $R^{1a}$;

$R^{1a}$ is selected from a group consisting of H, deuterium, halogen, cyano, alkyl, alkenyl, alkynyl, aryl, heteroaryl, cycloalkyl, and heterocycloalkyl, wherein said alkyl, alkenyl, alkynyl, aryl, heteroaryl, cycloalkyl, or heterocycloalkyl may be optionally substituted with halogen, cyano, $OR^a$, $SR^a$, $NR^bR^c$, alkyl, alkenyl, alkynyl, cycloalkyl, or heterocycloalkyl;

$R^2$ is selected from a group consisting of aryl, heteroaryl, cycloalkyl, and heterocycloalkyl, wherein $R^2$ may be optionally substituted with one to five $R^{2a}$;

$R^{2a}$ is selected from a group consisting of H, halogen, cyano, $OR^a$, $SR^a$, $NR^bR^c$, $NR^bC(O)R^d$, $NR^bC(O)OR^d$, $NR^b$-$C(O)NR^bR^c$, $NR^bS(O)_2R^d$, $NR^bS(O)_2NR^bR^c$, $C(O)NR^bR^c$, $(O)OR^d$, $S(O)_2NR^bR^c$, $C(O)R^d$, $S(O)_2R^d$, $P(O)R^bR^c$, alkyl, alkenyl, and alkynyl;

$R^3$ is selected from a group consisting of H, deuterium, alkyl, alkenyl, alkynyl, deuterated alkyl, haloalkyl, hydroxyalkyl, alkoxyalkyl, cyanoalkyl, cycloalkyl, and cycloalkylalkyl;

$R^4$ is selected from a group consisting of H, alkyl, hydroxyalkyl, alkoxyalkyl, haloalkyl, cyanoalkyl, cycloalkyl, and cycloalkylalkyl;

$R^5$ is selected from a group consisting of H, halogen, cyano, alkyl, alkenyl, alkynyl, aryl, heteroaryl, cycloalkyl, and heterocycloalkyl, wherein said alkyl, alkenyl, alkynyl, aryl, heteroaryl, cycloalkyl, or heterocycloalkyl may be substituted with one to three $R^{5a}$;

$R^{5a}$ is selected from a group consisting of H, deuterium, halogen, cyano, $OR^a$, $SR^a$, $NR^bR^c$, $NR^bC(O)R^d$, $NR^bC(O)OR^d$, $NR^bC(O)NR^bR^c$, $NR^bS(O)_2R^d$, $NR^bS(O)_2NR^bR^c$, $C(O)NR^bR^c$, $C(O)OR^d$, $S(O)_2NR^bR^c$, $C(O)R^d$, $S(O)_2R^d$, $P(O)R^bR^c$, alkyl, alkenyl, alkynyl, aryl, heteroaryl, cycloalkyl, and heterocycloalkyl;

$R^6$ and $R^7$ are each selected from a group consisting of H, amino, and alkyl;

$R^a$, $R^b$, $R^c$, and $R^d$ are independently selected from a group consisting of H, alkyl, haloalkyl, hydroxyalkyl, alkoxyalkyl, cyanoalkyl, alkenyl, alkynyl, cycloalkyl, heterocycloalkyl, aryl, and heteroaryl;

or $R^b$ and $R^c$, together with nitrogen atom(s) to which they are attached, form a four- to seven-membered heterocycloalkyl, and optionally substituted with one to three $R^e$; and $R^e$ is selected from a group consisting of H, halogen, cyano, $OR^a$, $SR^a$, $NR^bR^c$, $NR^bC(O)R^d$, $NR^bC(O)OR^d$, $NR^b$-$C(O)NR^bR^c$, $NR^bS(O)_2R^d$, $NR^bS(O)_2NR^bR^c$, $C(O)NR^bR^c$, $C(O)OR^d$, $S(O)_2NR^bR^c$, $C(O)R^d$, $S(O)_2R^d$, $P(O)R^bR^c$, alkyl, alkenyl, alkynyl, cycloalkyl, heterocycloalkyl, aryl, and heteroaryl.

Preferably, the present application provides a compound of Formula (II):

(II)

or a pharmaceutical salt thereof, wherein:

$R^1$ is selected from a group consisting of H, halogen, cyano, alkyl, alkenyl, alkynyl, aryl, heteroaryl, cycloalkyl, and heterocycloalkyl, wherein said alkyl, alkenyl, alkynyl, aryl, heteroaryl, cycloalkyl, or heterocycloalkyl may be optionally substituted with one to five $R^{1a}$;

$R^{1a}$ is selected from a group consisting of H, deuterium, halogen, cyano, alkyl, alkenyl, alkynyl, aryl, heteroaryl, cycloalkyl, and heterocycloalkyl, wherein said alkyl, alkenyl, alkynyl, aryl, heteroaryl, cycloalkyl, or heterocycloalkyl may be optionally substituted with halogen, cyano, $OR^a$, $SR^a$, $NR^bR^c$, alkyl, alkenyl, alkynyl, cycloalkyl, or heterocycloalkyl;

$R^{2a}$ is selected from a group consisting of H, halogen, cyano, $OR^a$, $SR^a$, $NR^bR^c$, $NR^bC(O)R^d$, $NR^bC(O)OR^d$, $NR^b$-$C(O)NR^bR^c$, $NR^bS(O)_2R^d$, $NR^bS(O)_2NR^bR^c$, $C(O)NR^bR^c$, $C(O)OR^d$, $S(O)_2NR^bR^c$, $C(O)R^d$, $S(O)_2R^d$, $P(O)R^bR^c$, alkyl, alkenyl, and alkynyl;

$R^3$ is selected from a group consisting of H, deuterium, alkyl, alkenyl, alkynyl, deuterated alkyl, haloalkyl, hydroxyalkyl, alkoxyalkyl, cyanoalkyl, cycloalkyl, and cycloalkylalkyl;

$R^6$ and W are each selected from a group consisting of H, amino, and alkyl;

$R^a$, $R^b$, $R^c$, and $R^d$ are independently selected from a group consisting of H, alkyl, haloalkyl, hydroxyalkyl, alkoxyalkyl, cyanoalkyl, alkenyl, alkynyl, cycloalkyl, heterocycloalkyl, aryl, and heteroaryl;

or $R^b$ and $R^c$, together with nitrogen atom(s) to which they are attached, form a four- to seven-membered heterocycloalkyl, and optionally substituted with one to three $R^e$;

$R^e$ is selected from a group consisting of H, halogen, cyano, $OR^a$, $SR^a$, $NR^bR^c$, $NR^bC(O)R^d$, $NR^bC(O)OR^d$, $NR^b$-$C(O)NR^bR^c$, $NR^bS(O)_2R^d$, $NR^bS(O)_2NR^bR^c$, $C(O)NR^bR^c$, $C(O)OR^d$, $S(O)_2NR^bR^c$, $C(O)R^d$, $S(O)_2R^d$, $P(O)R^bR^c$, alkyl, alkenyl, alkynyl, cycloalkyl, heterocycloalkyl, aryl, and heteroaryl; and n is 1, 2, or 3.

In a preferred embodiment, $R^1$ is selected from a group consisting of halogen, cyano, alkyl, haloalkyl, cycloalkyl, heterocycloalkyl, aryl, and heteroaryl.

In a more preferred embodiment, $R^1$ is selected from halogen.

In a preferred embodiment, $R^{2a}$ is selected from H and halogen.

In a more preferred embodiment, $R^{2a}$ is selected from H and fluorine.

In a preferred embodiment, $R^3$ is selected from a group consisting of alkyl, haloalkyl, and cycloalkyl.

In a more preferred embodiment, $R^3$ is selected from alkyl.

In a preferred embodiment, $R^4$ is selected from H and alkyl.

In a more preferred embodiment, $R^4$ is selected from H.

In a preferred embodiment, $R^5$ is selected from a group consisting of halogen, cyano, alkynyl, cycloalkylalkynyl, arylalkynyl, heteroarylalkynyl, aryl, and heteroaryl.

In a more preferred embodiment, $R^5$ is selected from cyano.

In a preferred embodiment, $R^6$ is selected from a group consisting of H, amino, and alkyl.

In a preferred embodiment, $R^7$ is selected from H and amino.

The term "halo" or "halogen" includes fluorine, chlorine, bromine and iodine.

The term "alkyl" refers to a straight-chain or branched saturated hydrocarbon group. Examples of alkyl include methyl (Me), ethyl (Et), propyl (such as n-propyl and isopropyl), butyl (such as n-butyl, isobutyl, tert-butyl), pentyl (such as n-pentyl, isopentyl, neopentyl), hexyl (such as n-hexyl, 2-hexyl, 3-hexyl, 2-methylpentyl, 3-methylpentyl, 2,2-dimethylbutyl, 3-ethylpentyl-1, etc.), heptyl (such as n-heptyl, 2-heptyl, 3-heptyl, 4-heptyl, 2-methylhexyl, 3-methylhexyl, 2,2-dimethylpentyl, 3,3-dimethylpentyl, 3-ethylpentyl-1, etc.), octyl (such as 1-octyl, 2-octyl, 2-ethylhexyl, etc.), nonyl (such as 1-nonyl), decyl (such as n-decyl), and similar groups. The term "alkyl" refers particularly to a straight-chain or branched alkyl having one to twenty carbon atoms, and more particularly to a straight-chain or branched alkyl having one to ten carbon atoms, and further preferably to a straight-chain or branched alkyl having one to six carbon atoms. Unless specified otherwise, the definitions of all the groups in the present application are as defined herein in this text.

The term "hydroxyalkyl" refers to an alkyl group substituted with a hydroxyl, wherein the alkyl group is as defined above.

The term "haloalkyl" refers to an alkyl group having one or more halogen substituents, wherein the alkyl group and halo or halogen are as defined above. Examples of haloalkyl include $CH_2F$, $CHF_2$, $CF_3$, $C_2F_5$, $CCl_3$, and similar groups.

The term "cyanoalkyl" refers to an alkyl group substituted with a cyano group (—CN).

The term "alkenyl" refers to a hydrocarbon group having one or more C=C double bonds. Examples of alkenyl include vinyl, propenyl, allyl, 1-butenyl, 2-butenyl, 1,3-butadienyl, 1-pentenyl, 2-pentenyl, 1,3-pentadienyl, 1-hexenyl, 2-hexenyl, etc., and similar groups.

The term "alkynyl" refers to a hydrocarbon group having one or more C≡C triple bonds. Examples of alkynyl include ethynyl, propynyl, propargyl, 1-butynyl, 2-butynyl, 1-pentynyl, 2-pentynyl, 1-hexynyl, 2-hexynyl, etc., and similar groups.

The term "cycloalkyl" refers to a non-aromatic carbocyclic ring, including a cyclized alkyl group, a cyclized alkenyl group, and a cyclized alkynyl group. Cycloalkyl group may be a monocyclic or polycyclic (for example having two, three, or four fused rings) system, including spiro rings. In certain embodiments, the cycloalkyl group may have three to twenty carbon atoms. Cycloalkyl group may further have zero, one, two, or three C=C double bonds and/or zero, one, or two C≡C triple bonds. Also included in the definition of cycloalkyl are moieties having one or more aromatic rings fused with a cycloalkyl ring (for example having a bond in common), such as benzo derivatives of pentane, pentene, hexane, hexene, and similar compounds. Cycloalkyl groups having one or more fused aromatic rings may be linked by an aromatic portion or a non-aromatic portion. Examples of cycloalkyl groups include cyclopropyl, cyclobutyl, cyclopentyl, cyclohexyl, cycloheptyl, cyclopentenyl, cyclohexenyl, cyclohexadienyl, cycloheptenyl, cycloheptadienyl, adamantyl, and similar groups.

The term "heterocycloalkyl" refers to a non-aromatic heterocyclic ring wherein one or more atoms forming the ring are heteroatoms such as O, N, S, or phosphorus. A heterocyclic group may include monocyclic or polycyclic (for example having two, three, or four fused rings) system and spiro rings. Preferably, examples of "heterocycloalkyl" include, but not limited to: aziridinyl (azacyclopropyl), azetidinyl (azacyclobutyl), tetrahydrofuranyl, tetrahydrothienyl, pyrrolidinyl, oxazolidinyl, thiazolidinyl, imidazolidinyl, isoxazolidinyl, isothiazolidinyl, pyrazolidinyl, morpholinyl, thiomorpholinyl, piperazinyl, piperidinyl, and similar groups. Also included in the definition of heterocycloalkyl are moieties having one or more aromatic rings fused with a non-aromatic heterocycloalkyl ring (for example having a bond in common), such as 2,3-dihydrobenzofuranyl, 1,3-benzodioxolyl, benzo-1,4-dioxanyl, phthalimido, naphthalimido, and similar groups. Heterocycloalkyl groups having one or more fused aromatic rings may be linked by an aromatic portion or a non-aromatic portion. Nitrogen and sulphur atoms in heterocycloalkyl may be present in an oxidized form.

The term "aryl" refers to a mono-ring or multi-ring (for example having two, three, or four fused rings) aromatic hydrocarbon, such as phenyl, naphthyl, anthryl, phenanthryl, indenyl, and similar groups.

The term "heteroaryl" refers to an aromatic heterocyclic ring having at least one heteroatom (such as O, N or S) ring members. A heteroaryl group includes a monocyclic or polycyclic (for example having two, three, or four fused rings) ring system. Any N atoms forming a ring in a heterocyclic group may also be oxidized to form N-oxide. Preferably, examples of "heteroaryl" include, but not limited to: pyridyl, pyrimidinyl, pyrazinyl, pyridazinyl, triazinyl, furanyl, thienyl, imidazolyl, triazolyl, tetrazolyl, thiazolyl, isothiazolyl, 1,2,4-thiadiazolyl, pyrrolyl, oxazolyl, isoxazolyl, oxadiazolyl, benzofuranyl, benzothienyl, benzothiazolyl, indolyl, indazolyl, quinolyl, isoquinolyl, purinyl, carbazolyl, benzoimidazolyl, pyrropyridyl, pyrropyrimidinyl, pyrazolopyridyl, pyrazolopyrimidinyl, and similar groups.

The term "compound", as used herein, is meant to include all stereoisomers, geometric isomers, tautomers, and isotopes.

The compound of the present application may be asymmetric, for example, having one or more stereocenters. Unless specified otherwise, all stereoisomers are, for example, enantiomers and diastereoisomers. The compound of the present application having asymmetrically substituted carbon atoms may be isolated in optically active or racemic forms. The optically active forms may be prepared by resolution of racemic mixtures, or by using chiral synthon or a chiral reagent.

The compound of the present application may also include tautomeric forms. New tautomeric forms result from the exchange of a single bond with an adjacent double bond together with the migration of a proton.

The compound of the present application may also include all isotopic forms of atoms present in an intermediate or a final compound. Isotopes include those atoms having the same atomic number but different mass numbers. For example, isotopes of hydrogen include deuterium and tritium.

The present application further includes a pharmaceutical salt of the compound of Formula (I). A pharmaceutical salt refers to a derivative of the compound in which the parent compound is modified by converting a base moiety to its salt form, or a derivative of the compound in which the parent compound is modified by converting an acid moiety to its salt form. Examples of the pharmaceutical salt include, but not limited to, inorganic or organic acid salts of basic groups (such as amines), or inorganic or organic base salts of acidic groups (such as carboxylic acids). The pharmaceutical salt of the present application may be synthesized by causing a free base form of the parent compound of Formula (I) to react with 1-4 equivalent of a suitable acid in a solvent system. Suitable salts are listed in *Remington's Pharmaceutical Sciences,* 17$^{th}$ ed., Mack Publishing Company, Easton, Pa., 1985, p. 1418 and *Journal of Pharmaceutical Science,* 66, 2 (1977).

The compound of the present application and its pharmaceutical salt further include solvate forms or hydrate forms. Generally speaking, solvate forms or hydrate forms and non-solvate forms or non-hydrate forms are equivalent, and both are included in the scope of the present application. Some compounds of the present application may be present in various crystalline forms or amorphous forms. In general, all physical forms of the compounds are included in the scope of the present application.

The present application further includes a prodrug of the compound of Formula (I). A prodrug is a pharmacological substance (namely a drug) that is derived from a parent drug. After administration, the prodrug is metabolized into the parent drug in vivo. A prodrug may be prepared by substituting one or more functional groups in a compound, wherein a substituent in the prodrug is removed in vivo in such a way that the prodrug converts to the parent compound. The preparation and use of a prodrug may be found in T. Higuchi and V. Stella, "Pro-drugs as Novel Delivery Systems," Vol. 14 of the A.C.S. Symposium Series and *Bioreversible Carriers in Drug Design*, ed. Edward B. Roche, American Pharmaceutical Association and Pergamon Press, 1987.

The present application further provides a composition including the compound of Formula (I), and a pharmaceutical carrier or excipient. The composition of the present application may be administered orally, parenterally (by injection), by spray inhalation, topical administration, rectal administration, nasal administration, vaginal administration, intraperitoneal administration, or via an implanted reservoir.

The present application, in another aspect, provides a method of regulating kinase activity using the compound of Formula (I). As used herein, the term "regulating kinase activity" refers to reduced kinase activity when contacted with the compound of Formula (I) of the present application, relative to kinase activity in the absence of the compound of Formula (I). The present application therefore provides a method of regulating activity of a kinase by contacting the kinase with the compound of Formula (I) of the present application.

In some embodiments, the kinase is a lipid kinase, such as PI3Kα, PI3Kβ, PI3Kγ, or PI3Kδ.

In some embodiments, the kinase is PI3Kδ.

The present application, in further another aspect, provides a method of treating PI3K mediated diseases using the compound of the present application. The PI3K related diseases include cancers, inflammatory diseases, and autoimmune diseases.

In some embodiments, the cancers described in the present application are solid tumor, leukemia, lymphoma, and multiple myeloma.

In some embodiments, the leukemia described in the present application is selected from a group consisting of acute lymphocytic leukemia (ALL), acute myeloid leukemia (AML), chronic lymphocytic leukemia (CLL), and chronic myeloid leukemia (CML). The lymphoma is selected from a group consisting of Hodgkin's leukemia, non-Hodgkin's leukemia (NHL), mantle cell leukemia (MCL), follicular leukemia, B-cell lymphoma, T-cell lymphoma, and diffuse large B-cell lymphoma.

In some embodiments, the autoimmune diseases and the inflammatory diseases are selected from a group consisting of dermatitis, rheumatoid arthritis, allergic rhinitis, asthma, Crohn's disease, chronic obstructive pulmonary disease (COPD), systemic lupus erythematosus, psoriasis, multiple sclerosis, activated PI3Kδ syndrome, and Sjogren syndrome.

The present application, in another aspect, provides use of the compound or the pharmaceutical salt thereof or the pharmaceutical composition of the present application combined with one or more drugs, for treating cancers, inflammatory diseases, and autoimmune diseases.

In some embodiments, the drugs used in combination include a small molecule compound and a macromolecule antibody drug. The small molecule compound is selected from, but not limited to, various kinase inhibitors such as BTK inhibitors and other small molecule non-kinase inhibitors and so on. The macromolecule antibody drug includes anti-CD20, anti-CTLA4, anti-PD-1, and anti-PD-L1 and so on.

The present application, in further another aspect, provides a method of preparing the compound of Formula (I). The compound of the present application may be prepared by reaction scheme and methods described below.

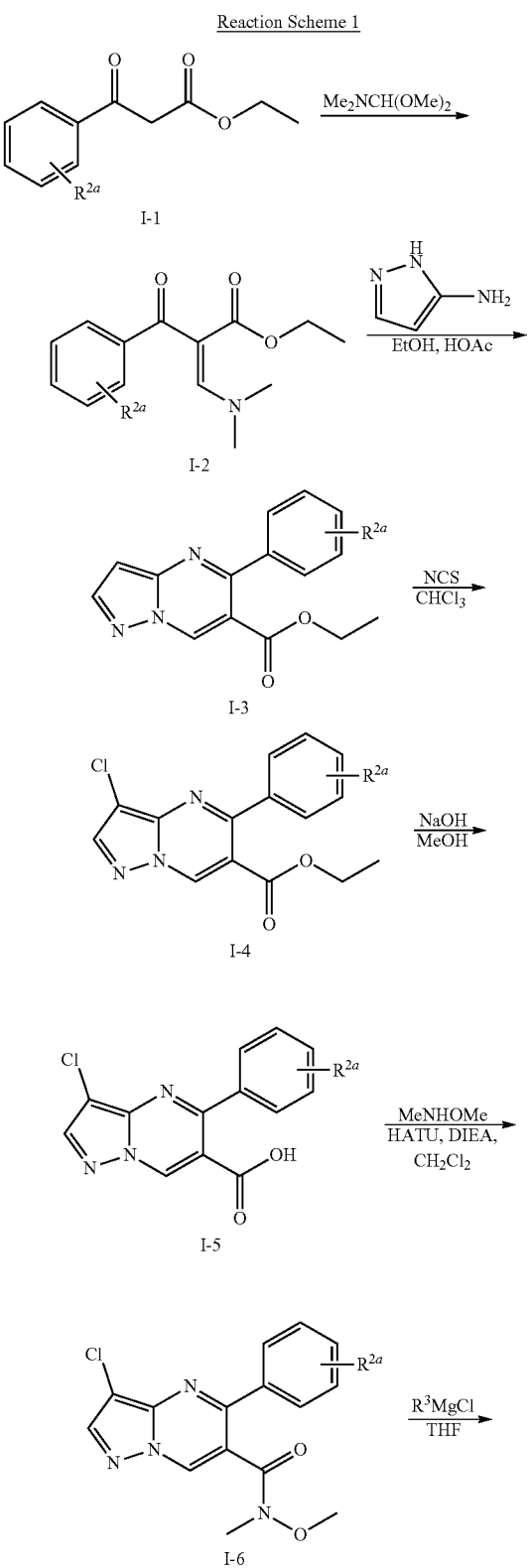

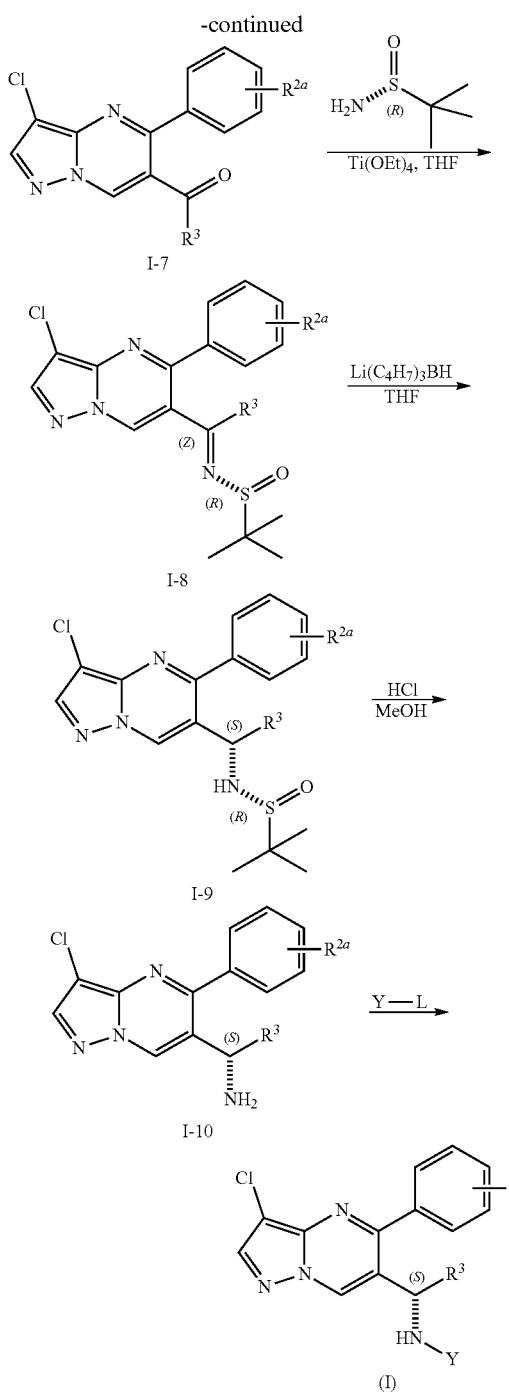

ketone I-7. Ketone I-7 and (R)-sulfenamide are subjected to a condensation reaction to obtain compound I-8. The imino group in compound I-8 is reduced by tri-sec-butyl lithium borohydride to obtain S-configuration sulfonamide compound I-9. The sulphinyl in the compound I-9 is removed by hydrochloric acid to obtain free amine I-10. Free amine I-10 reacts with Y-L (Y being pyrimidine substituted with $R^5$, $R^6$, and $R^7$, and L being a leaving group) to obtain a final product (I).

DETAILED DESCRIPTION

The following embodiments are used for illustrating preferred embodiments of the present application. Those persons skilled in the art shall appreciate that the techniques disclosed in the following embodiments are techniques discovered by the inventor of the present application and playing an excellent role in the embodiments of the present application, and therefore can be considered to constitute the preferred embodiments of the present application. However, based on the contents disclosed in the present application, those persons skilled in the art shall appreciate that, without departing from the spirit and scope of the present application, various variations may be made to the disclosed specific embodiments to achieve similar or same results.

Example 1

(S)-4-amino-6-(1-(3-chloro-5-phenylpyrazolo[1,5-a]pyrimidin-6-yl)ethylamino) pyrimidin-5-carbonitrile

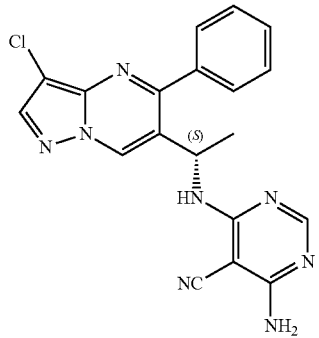

Step 1. ethyl 5-phenylpyrazolo[1,5-a]pyrimidin-6-carboxylate

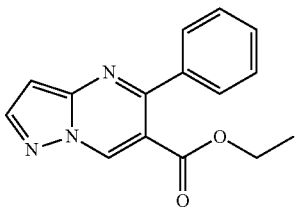 [SMILES: CCOC(=O)c1cn2nccc2nc1-c1ccccc1]

To a 250-mL round-bottom flask were added ethyl benzoylformate (10 g, 56.2 mmol), N,N-dimethylformamide dimethyl acetal (6.7 g, 56.2 mmol), and 120 mL of toluene for a reflux reaction for 2 hours. After completion of the reaction, the resultant mixture was subjected to reduced pressure distillation to remove toluene. The resulting residue was dissolved in 200 mL of ethanol to obtain a solution. To this solution were added 3-aminopyrazole (4.7 g, 56.6 mmol) and 40 mL of glacial acetic acid under stirring, followed by a reaction at room temperature for 8 hours. After the reaction was finished, the resultant mixture was subjected to reduced pressure distillation to remove ethanol to obtain a residue. The residue was diluted by an addition of $H_2O$, and was then extracted with $CH_2Cl_2$. The resultant organic phase was washed in sequence with a saturated $Na_2CO_3$ solution and a saturated NaCl solution, dried with anhydrous $Na_2SO_4$, and then filtered and concentrated to obtain a yellow solid of 14.2 g for direct use in a next reaction step. The yield was 94%. LCMS (ESI): m/z=268 $(M+H)^+$.

Step 2. ethyl 3-chloro-5-phenylpyrazolo[1,5-a]pyrimidin-6-carboxylate

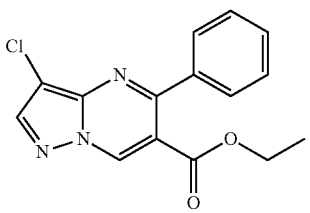 [SMILES: CCOC(=O)c1cn2ncc(Cl)c2nc1-c1ccccc1]

Ethyl 5-phenylpyrazolo[1,5-a]pyrimidin-6-carboxylate (14.2 g, 53.1 mmol) was dissolved in 150 mL of $CHCl_3$, followed by an addition of NCS (7.1 g, 53.2 mmol). The resultant mixture was heated to 60° C. to react for 6 hours. After the completion of the reaction, the resultant mixture was diluted with $CH_2Cl_2$, and then washed in sequence with 0.1 N HCl aqueous solution and a saturated NaCl solution. The resultant organic phase was dried with anhydrous $Na_2SO_4$, and filtered and concentrated to obtain a yellow solid of 15.5 g for direct use in a next reaction step. The yield was 97%. LCMS (ESI): m/z=302 $(M+H)^+$.

Step 3. ethyl 3-chloro-5-phenylpyrazolo[1,5-a]pyrimidin-6-carboxylate

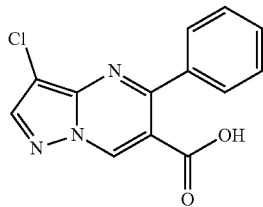 [SMILES: O=C(O)c1cn2ncc(Cl)c2nc1-c1ccccc1]

To a 250-mL round-bottom flask were added ethyl 3-chloro-5-phenylpyrazolo[1,5-a]pyrimidine-6-carboxylate (15.5 g, 51.5 mmol), 50 mL of methanol, and 100 mL of 2 N NaOH aqueous solution to react at room temperature for 5 hours. After the completion of the reaction, the resultant mixture was subjected to reduced pressure distillation to remove methanol, and then filtered to obtain a filter residue and a filtrate. The filter residue was washed with $H_2O$. The filtrate was adjusted using 4 N HCl aqueous solution to have a pH value of 3 to precipitate a solid and then filtered to obtain a solid of 8.2 g. The yield was 58%. LCMS (ESI): m/z=274 $(M+H)^+$.

Step 4. 3-chloro-N-methoxy-N-methyl-5-phenylpyrazolo[1,5-a]pyrimidin-6-amide

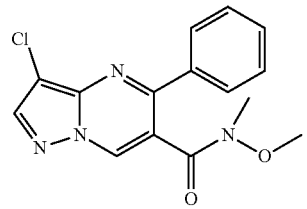 [SMILES: CON(C)C(=O)c1cn2ncc(Cl)c2nc1-c1ccccc1]

3-chloro-5-phenylpyrazolo[1,5-a]pyrimidin-6-carboxylic acid (8.2 g, 30 mmol) and DIEA (11.6 g, 90 mmol) were dissolved in 100 mL of $CH_2Cl_2$, followed by an addition of N,O-dimethylhydroxylamine hydrochloride (3.2 g, 33 mmol) and HATU (12.5 g, 33 mmol) for reaction at room temperature for 2 hours. After the completion of the reaction, the resultant mixture was diluted with $CH_2Cl_2$. The resultant organic phase was washed with a saturated NaCl solution, dried with anhydrous $Na_2SO_4$, filtered, and concentrated to obtain a residue. The residue was purified by column chromatography (PE:EtOAc (v/v)=2:1) to obtain a solid of 8.5 g. The yield was 90%. LCMS (ESI): m/z=317 $(M+H)^+$.

Step 5. 1-(3-chloro-5-phenylpyrazolo[1,5-a]pyrimidine-6-yl) ethanone

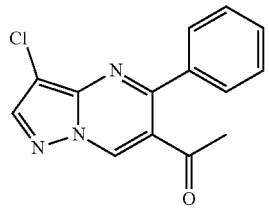 [SMILES: CC(=O)c1cn2ncc(Cl)c2nc1-c1ccccc1]

Under an atmosphere of nitrogen, 3-chloro-N-methoxy-N-methyl-5-phenylpyrazolo[1,5-a]pyrimidin-6-amide (8.5 g, 26.9 mmol) was dissolved in 80 mL of THF, and was then placed and cooled in an ice-bath. To the upper solution was slowly added dropwise methylmagnesium chloride in THF (3M, 14 mL), and the addition was completed in 20 minutes. After the completion of the dropwise addition, the resultant mixture was maintained at the temperature for reaction for 1 hour. After the reaction was finished, a saturated $NH_4Cl$ solution was carefully added to the resultant mixture to quench the reaction, and the resultant mixture was subjected to reduced pressure distillation to remove THF. The resultant aqueous phase was extracted with EtOAc. The organic phases were combined and then washed with a saturated NaCl solution, dried with anhydrous $Na_2SO_4$, filtered, and then concentrated to obtain a solid of 6.5 g. The yield was 89%. LCMS (ESI): m/z=272 $(M+H)^+$.

Step 6. (R,E)-N-(1-(3-chloro-5-phenylpyrazolo[1,5-a]pyrimidin-6-yl) ethylidene)-2-methylpropan-2-sulfonamide

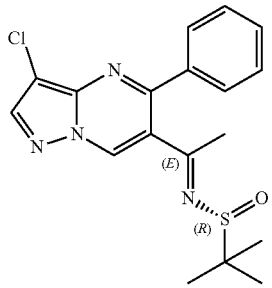

(R)-tert-butylsulfenamide (3 g, 24.8 mmol) was dissolved in 30 mL of THF, followed by a dropwise addition of a THF solution (50 mL) containing 1-(3-chloro-5-phenylpyrazolo[1,5-a]pyrimidin-6-yl)ethanone (6.5 g, 24 mmol) and tetraethyl titanate (11 g, 48.2 mmol). The resultant mixture was heated for a reflux reaction for 4 hours. After the completion of the reaction, the resultant mixture was cooled to room temperature, followed by an addition of a saturated NH$_4$Cl solution. The resultant mixture was subjected to reduced pressure distillation to remove THF. The resultant aqueous phase was extracted with EtOAc. The organic phases were combined and then washed with a saturated NaCl solution, dried with anhydrous Na$_2$SO$_4$, filtered, and then concentrated to obtain a residue. The residue was purified by column chromatography (PE:EtOAc (v/v)=1:1) to obtain a solid of 4.2 g. The yield was 45%. LCMS (ESI): m/z=375 (M+H)$^+$.

Step 7. (R)—N—((S)-1-(3-chloro-5-phenylpyrazolo[1,5-a]pyrimidin-6-yl) ethyl)-2-methylpropan-2-sulfenamide

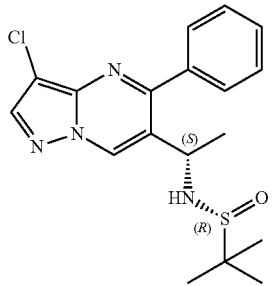

Under an atmosphere of nitrogen, (R,E)-N-(1-(3-chloro-5-phenylpyrazolo[1,5-a]pyrimidin-6-yl)ethylidene)-2-methylpropan-2-sulfenamide (4.2 g, 11.2 mmol) was dissolved in 40 mL of THF, cooled to −40° C., and maintained at −40° C., followed by a dropwise addition of a THF solution (1 M, 22 mL) containing lithium tri-sec-butylborohydride. After the dropwise addition, the resultant mixture was maintained at the temperature for reaction for 1 hour. After the completion of the reaction, a saturated NH$_4$Cl solution was added and stirred for 5 minutes. The resultant mixture was heated to room temperature, subjected to reduced pressure distillation to remove THF. The resultant aqueous phase was extracted with EtOAc. The organic phases were combined and then washed with a saturated NaCl solution, dried with anhydrous Na$_2$SO$_4$, filtered, and then concentrated to obtain a residue. The residue was purified by column chromatography (PE:EtOAc (v/v)=1:1) to obtain a solid of 2 g. The yield was 47%. LCMS (ESI): m/z=377 (M+H)$^+$.

Step 8. (S)-1-(3-chloro-5-phenylpyrazolo[1,5-a]pyrimidin-6-yl)ethylamine

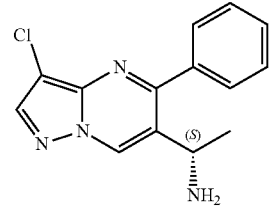

(R)—N—(S)-1-(3-chloro-5-phenylpyrazolo[1,5-a]pyrimidin-6-yl)ethyl)-2-methylpropan-2-sulfenamide (2 g, 5.3 mmol) was dissolved in 10 mL of MeOH, followed by an addition of concentrated hydrochloric acid (4 mL), for reaction for 1 hour under stirring at room temperature. After the completion of the reaction, the resultant mixture was placed and cooled in an ice-bath, adjusted by using a saturated Na$_2$CO$_3$ solution to have a pH value of 9, and subjected to reduced pressure distillation to remove methanol. The resultant aqueous phase was extracted with EtOAc. The organic phases were combined and then washed with a saturated NaCl solution, dried with anhydrous Na$_2$SO$_4$, filtered, and then concentrated to obtain a solid of 1.2 g. The yield was 83%. LCMS (ESI): m/z=273 (M+H)$^+$.

Step 9. (S)-4-amino-6-(1-(3-chloro-5-phenylpyrazolo[1,5-a]pyrimidin-6-yl) ethylamino)pyrimidin-5-carbonitrile

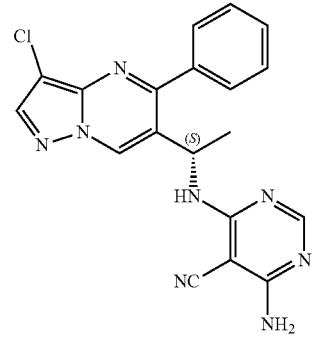

To a 25-mL round-bottom flask were added (S)-1-(3-chloro-5-phenylpyrazolo[1,5-a]pyrimidin-6-yl)ethylamine (150 mg, 0.55 mmol), 4-amino-5-nitrile-6-chloropyrimidine (85 mg, 0.55 mmol), KF (64 mg, 1.1 mmol), DIEA (355 mg, 2.75 mmol), and DMSO (5 mL), and the resulted mixture was heated to 90° C. for reaction for 2 hours. After the completion of the reaction, the resultant mixture was diluted with H$_2$O and extracted with EtOAc. The organic phases were combined and then washed with a saturated NaCl solution, dried with anhydrous Na$_2$SO$_4$, filtered, and then concentrated to obtain a residue. The residue was purified by column chromatography (PE:EtOAc (v/v)=1:1) to obtain a solid of 178 mg. The yield was 83%. LCMS (ESI): m/z=391 (M+H)$^+$. $^1$H NMR (400 MHz, CDCl$_3$) δ 8.69 (s, 1H), 8.03 (s, 1H), 8.01 (s, 1H), 7.84-7.69 (m, 1H), 7.66-7.55 (m, 3H), 7.52-7.32 (m, 1H), 5.59 (d, J=6.2 Hz, 1H), 5.51 (s, 2H), 5.26-5.14 (m, 1H), 1.57 (d, J=7.1 Hz, 3H).

Example 2

(S)-2,4-diamino-6-(1-(3-chloro-5-phenylpyrazolo[1,5-a]pyrimidin-6-yl)ethylamino)pyrimidin-5-carbonitrile

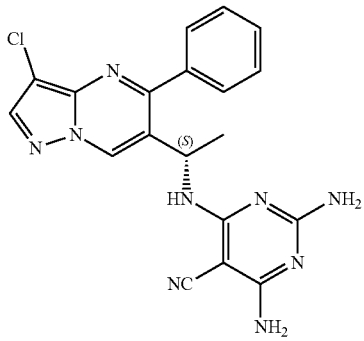

Step 1. 2,4,6-trichloropyrimidin-5-carboxaldehyde

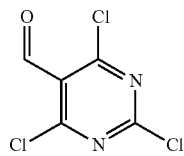 [SMILES: O=Cc1c(Cl)nc(Cl)nc1Cl]

POCl$_3$ (76.5 g, 0.5 mmol) was added to a 150-mL round-bottom flask, and then placed and cooled in an ice-bath, followed by a dropwise addition of DMF (5.7 g, 78 mmol). The resultant mixture was maintained at the temperature for reaction for 20 minutes. Barbituric acid (10 g, 78 mmol) was added to the upper solution, and the ice-bath was removed. The resultant mixture was heated for a reflux reaction for 12 hours. After completion of the reaction, the resultant mixture was subjected to reduced pressure distillation to remove the remaining POCl$_3$. The residue was added to crushed ice and was extracted with EtOAc. Organic phases were combined, washed with a saturated NaCl solution, dried with anhydrous Na$_2$SO$_4$, and then filtered and concentrated to obtain an oily substance of 10 g for direct use in a next reaction step. The yield was 61%.

Step 2. 2,4,6-trichloropyrimidin-5-carbonitrile

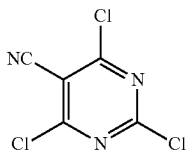 [SMILES: N#Cc1c(Cl)nc(Cl)nc1Cl]

2,4,6-trichloropyrimidin-5-carboxaldehyde (10 g, 47.4 mmol), hydroxylamine hydrochloride (3.3 g, 47.5 mmol), glacial acetic acid (100 mL), and H$_2$O (5 mL) were added to a 150-mL round-bottom flask, and heated to 60° C. to react for 1 hour. After the completion of the reaction, the reaction solution was poured into crushed ice, and was extracted with CH$_2$Cl$_2$. The resultant organic phases were combined, washed with a saturated NaCl solution, dried with anhydrous Na$_2$SO$_4$, and then filtered and concentrated. The obtained substance was dissolved in SOCl$_2$ (60 mL), reacted at room temperature for 10 minutes, and then heated for a reflux reaction for 2 hours. After the completion of the reaction, the resultant mixture was subjected to reduced pressure distillation to remove SOCl$_2$ to give a residue, which was then dissolved in EtOAc and washed with H$_2$O. The resultant organic phase was dried with anhydrous Na$_2$SO$_4$, filtered, and concentrated to obtain an oily substance of 9 g. The yield was 92%.

Step 3. 2,4-diamino-6-chloropyrimidin-5-carbonitrile

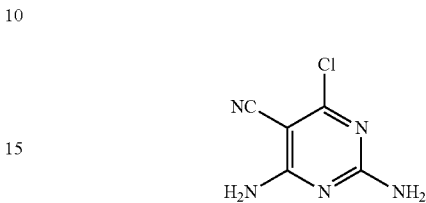

2,4,6-trichloropyrimidin-5-carbonitrile (9 g, 43.5 mmol), dioxane (40 mL), and ammonium hydroxide (36%, 40 mL) were added to a 150-mL round-bottom flask, and heated to 50° C. to react for 1 hour. After the completion of the reaction, the resultant mixture was cooled to room temperature, followed by an addition of 50 mL of ice water, and then placed and cooled in an ice-bath and stirred for 1.5 hours. The resultant mixture was filtered to obtain a filter residue. The filter residue was washed with H$_2$O to obtain a light yellow solid of 3.8 g. The yield was 51%. LCMS (ESI): m/z=170 (M+H)$^+$.

Step 4. (S)-2,4-diamino-6-(1-(3-chloro-5-phenylpyrazolo[1,5-a]pyrimidin-6-yl) ethylamino)pyrimidin-5-carbonitrile

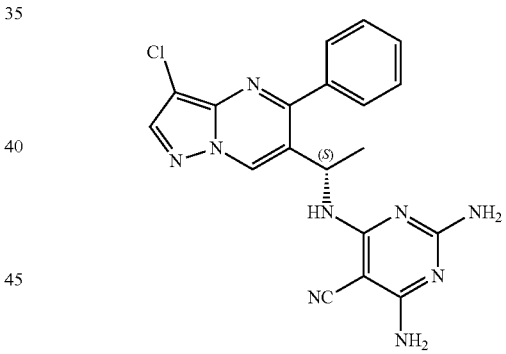

(S)-1-(3-chloro-5-phenylpyrazolo[1,5-a]pyrimidin-6-yl)ethylamine (150 mg, 0.55 mmol), 2,4-diamino-6-chloropyrimidin-5-carbonitrile (93 mg, 0.55 mmol), KF (64 mg, 1.1 mmol), DIEA (355 mg, 2.75 mmol), and DMSO (5 mL) were added to a 25-mL round-bottom flask, and heated to 90° C. to react for 2 hours. After the completion of the reaction, the resultant mixture was diluted with H$_2$O, and extracted with EtOAc. The organic phases were combined, washed with a saturated NaCl solution, dried with anhydrous Na$_2$SO$_4$, filtered, and then concentrated to obtain a residue. The residue was purified by column chromatography (PE:EtOAc (v/v)=1:1) to obtain a solid of 156 mg. The yield was 70%. LCMS (ESI): m/z=406 (M+H)$^+$. $^1$H NMR (400 MHz, CDCl$_3$) δ 8.71 (s, 1H), 8.02 (s, 1H), 7.79-7.69 (m, 1H), 7.69-7.56 (m, 3H), 7.50-7.38 (m, 1H), 5.47 (d, J=6.7 Hz, 1H), 5.31-5.08 (m, 3H), 4.80 (s, 2H), 1.57 (d, J=7.1 Hz, 3H).

Example 3

(S)-2,4-diamino-6-(1-(3-chloro-5-(3-fluorophenyl)pyrazolo[1,5-a]pyrimidin-6-yl) ethylamino)pyrimidin-5-carbonitrile

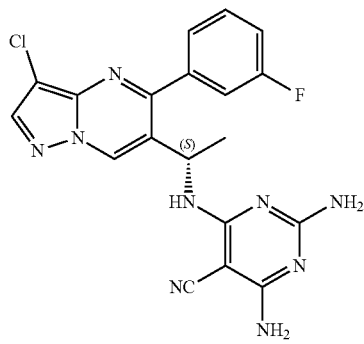

Step 1. ethyl 3-(3-fluorophenyl)-3-oxopropanoate

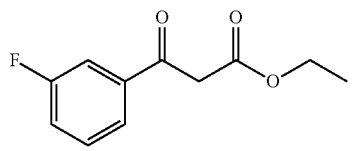

Potassium tert-butoxide (20 g, 178.6 mmol) was dissolved in 200 mL of THF, and cooled to −20° C., followed by a dropwise addition of ethyl 3-fluorobenzoate (10 g, 59.5 mmol), maintained at the temperature and reacted for 30 minutes. Then, ethyl acetate (15.7 g, 178.4 mmol) was slowly added dropwise, after which the resultant mixture was maintained at the temperature and reacted for 1 hour. After the completion of the reaction, 3 N HCl aqueous solution (75 mL) was added, and the resultant mixture was subjected to reduced pressure distillation to remove THF. The resultant aqueous phase was extracted with EtOAc. The organic phases were combined, washed in sequence with a saturated $Na_2CO_3$ solution and a saturated NaCl solution, dried with anhydrous $Na_2SO_4$, filtered and concentrated to obtain an oily substance of 5 g for direct use in a next reaction step. The yield was 40%. LCMS (ESI): m/z=211 $(M+H)^+$.

Step 2. ethyl 5-(3-fluorophenyl)pyrazolo[1,5-a]pyrimidin-6-carboxylate

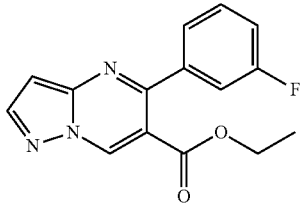 [SMILES: CCOC(=O)c1cn2nccc2nc1-c1cccc(F)c1]

Ethyl 3-(3-fluorophenyl)-3-oxopropanoate (5 g, 23.8 mmol), N,N-dimethylformamide dimethyl acetal (2.9 g, 24.4 mmol), and 50 mL of toluene were added to a 250-mL round-bottom flask for a reflux reaction for 2 hours. After the completion of the reaction, the resultant mixture was subjected to reduced pressure distillation to remove methylbenzene. The resultant residue was dissolved in 100 mL of ethanol, followed by an addition of 3-aminopyrazole (2 g, 24 mmol) and 20 mL of glacial acetic acid under stirring, and then reacted for 8 hours at room temperature. After the reaction was finished, the resultant mixture was subjected to reduced pressure distillation to remove ethanol to obtain a residue. The residue was diluted by an addition of $H_2O$, and then extracted with $CH_2Cl_2$. The resultant organic phase was washed in sequence with a saturated $Na_2CO_3$ solution and a saturated NaCl solution, dried with anhydrous $Na_2SO_4$, and then filtered and concentrated to obtain a yellow solid of 4.3 g for direct use in a next reaction step. The yield was 63%. LCMS (ESI): m/z=286 $(M+H)^+$.

Step 3. ethyl 3-chloro-5-(3-fluorophenyl)pyrazolo[1,5-a]pyrimidin-6-carboxylate

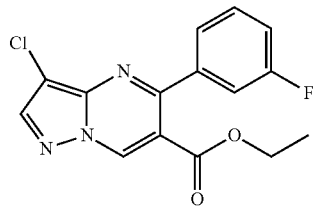 [SMILES: CCOC(=O)c1cn2ncc(Cl)c2nc1-c1cccc(F)c1]

Ethyl 5-(3-fluorophenyl)pyrazolo[1,5-a]pyrimidine-6-carboxylate (4.3 g, 15.1 mmol) was dissolved in 50 mL of $CHCl_3$, followed by an addition of NCS (2.1 g, 15.7 mmol). The resultant mixture was heated to 60° C. to react for 6 hours. After the completion of the reaction, the resultant mixture was diluted with $CH_2Cl_2$, and then washed in sequence with 0.1 N HCl aqueous solution and a saturated NaCl solution.

The resultant organic phase was dried with anhydrous $Na_2SO_4$, and filtered and concentrated to obtain a yellow solid of 4.6 g for direct use in a next reaction step. The yield was 95%. LCMS (ESI): m/z=320 $(M+H)^+$.

Step 4. 3-chloro-5-(3-fluorophenyl)pyrazolo[1,5-a]pyrimidin-6-carboxylic acid

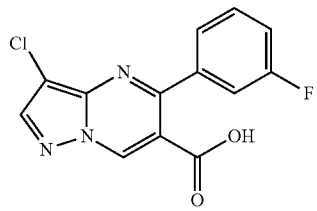 [SMILES: O=C(O)c1cn2ncc(Cl)c2nc1-c1cccc(F)c1]

Ethyl 3-chloro-5-(3-fluorophenyl)pyrazolo[1,5-a]pyrimidin-6-carboxylate (4.6 g, 14.4 mmol), 20 mL of methanol, and 60 mL of 2 N NaOH aqueous solution were added to a 100-mL round-bottom flask for reaction at room temperature for 5 hours. After the completion of the reaction, the resultant mixture was subjected to reduced pressure distillation to remove methanol, and then filtered to obtain a filter residue and a filtrate. The filter residue was washed with $H_2O$. The filtrate was adjusted using 4 N HCl solution to have a pH value of 3 to precipitate a solid and then filtered to obtain a solid of 2.3 g. The yield was 55%. LCMS (ESI): m/z=292 $(M+H)^+$.

Step 5. 3-chloro-5-(3-fluorophenyl)-N-methoxy-N-methyl-pyrazolo [1,5-a]pyrimidin-6-amide

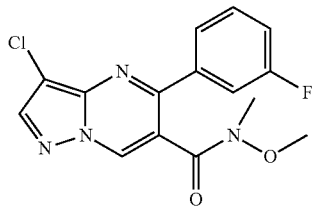 [SMILES: CON(C)C(=O)c1cn2ncc(Cl)c2nc1-c1cccc(F)c1]

Step 7. (R,E)-N-(1-(3-chloro-5-(3-fluorophenyl)pyrazolo[1,5-a]pyrimidin-6-yl) ethylidene)-2-methylpropan-2-sulfenamide

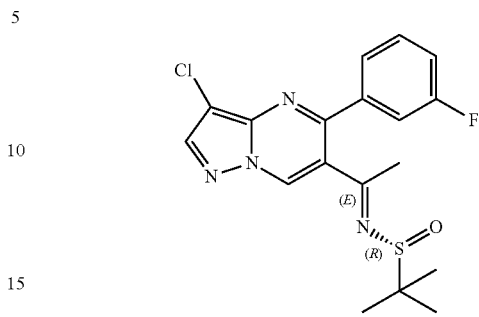

3-chloro-5-(3-fluorophenyl)pyrazolo[1,5-a]pyrimidin-6-carboxylic acid (2.3 g, 7.9 mmol), and DIEA (3 g, 23.3 mmol) were dissolved in 20 mL of $CH_2Cl_2$, followed by an addition of N,O-dimethylhydroxylamine hydrochloride (850 mg, 8.7 mmol) and HATU (3.3 g, 8.7 mmol) under stirring for reaction at room temperature for 2 hours. After the completion of the reaction, the resultant mixture was diluted with $CH_2Cl_2$. The resultant organic phase was washed with a saturated NaCl solution, dried with anhydrous $Na_2SO_4$, filtered, and concentrated to obtain a residue. The residue was purified by column chromatography (PE:EtOAc (v/v)=2:1) to obtain a solid of 2 g. The yield was 76%. LCMS (ESI): m/z=335 (M+H)+.

Step 6. 1-(3-chloro-5-(3-fluorophenyl)pyrazolo[1,5-a]pyrimidin-6-yl)ethanone

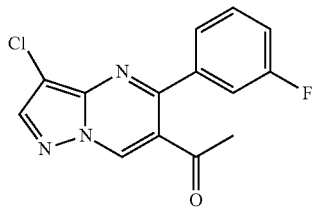 [SMILES: CC(=O)c1cn2ncc(Cl)c2nc1-c1cccc(F)c1]

Under nitrogen atmosphere, 3-chloro-5-(3-fluorophenyl)-N-methoxy-N-methylpyrazolo[1,5-a]pyrimidin-6-amide (2 g, 6 mmol) was dissolved in 20 mL of THF, and was then placed and cooled in an ice-bath. A solution of methylmagnesium chloride in THF (3M, 3 mL) was added slowly dropwise to the upper solution, and the addition was completed in 20 minutes. After the completion of the dropwise addition, the resultant mixture was maintained at the temperature and reacted for 1 hour. After the reaction was finished, a saturated $NH_4Cl$ solution was carefully added to the resultant mixture to quench the reaction, and the resultant mixture was subjected to reduced pressure distillation to remove THF. The resultant aqueous phase was extracted with EtOAc. The organic phases were combined and then washed with a saturated NaCl solution, dried with anhydrous $Na_2SO_4$, filtered, and then concentrated to obtain a solid of 1.5 g. The yield was 87%. LCMS (ESI): m/z=290 (M+H)+.

(R)-tert-butylsulfenamide (692 mg, 5.7 mmol) was dissolved in 10 mL of THF, followed by a dropwise addition of 1-(3-chloro-5-(3-fluorophenyl)pyrazolo [1,5-a]pyrimidin-6-yl)ethanone (1.5 g, 5.2 mmol) and a solution of tetraethyl titanate (2.4 g, 10.5 mmol) in THF (20 mL). The resultant mixture was heated for a reflux reaction for 4 hours. After the completion of the reaction, the resultant mixture was cooled to the room temperature, followed by an addition of a saturated $NH_4Cl$ solution. The resultant mixture was subjected to reduced pressure distillation to remove THF. The resultant aqueous phase was extracted with EtOAc. The organic phases were combined and then washed with a saturated NaCl solution, dried with anhydrous $Na_2SO_4$, filtered, and then concentrated to obtain a residue. The residue was purified by column chromatography (PE:EtOAc (v/v)=1:1) to obtain a solid of 840 mg. The yield was 41%. LCMS (ESI): m/z=393 (M+H)+.

Step 8. (R)—N—((S)-1-(3-chloro-5-(3-fluorophenyl) pyrazolo[1,5-a]pyrimidin-6-yl) ethyl)-2-methylpropan-2-sulfenamide

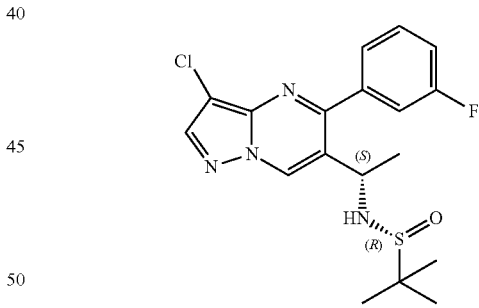

Under nitrogen atmosphere, (R,E)-N-(1-(3-chloro-5-(3-fluorophenyl)pyrazolo[1,5-a]pyrimidin-6-yl)ethylidene)-2-methylpropan-2-sulfenamide (840 mg, 2.14 mmol) was dissolved in 10 mL of THF, and cooled to −40° C. The resultant mixture was maintained at the temperature, followed by a dropwise addition of a solution of lithium tri-sec-butylborohydride in THF (1 M, 4.3 mL). After the dropwise addition, the resultant mixture was maintained at the temperature for reaction for 1 hour. After the completion of the reaction, a saturated $NH_4Cl$ solution was added and stirred for 5 minutes. The resultant mixture was heated to room temperature, subjected to reduced pressure distillation to remove THF. The resultant aqueous phase was extracted with EtOAc. The organic phases were combined and then washed with a saturated NaCl solution, dried with anhydrous Na₂SO₄, filtered, and then concentrated to obtain a residue. The residue was purified by column chromatography (PE: EtOAc (v/v)=1:1) to obtain a solid of 600 mg. The yield was 71%. LCMS (ESI): m/z=395 (M+H)⁺.

Step 9. (S)-1-(3-chloro-5-(3-fluorophenyl)pyrazolo[1,5-a]pyrimidin-6-yl)ethylamine

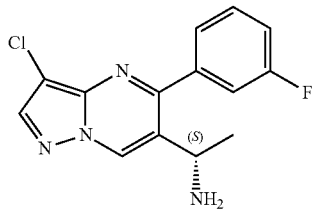

(R)—N—(S)-1-(3-chloro-5-(3-fluorophenyl)pyrazolo[1,5-a]pyrimidin-6-yl)ethyl)-2-methylpropan-2-sulfenamide (600 mg, 1.52 mmol) was dissolved in 5 mL of MeOH, followed by an addition of concentrated hydrochloric acid (2 mL), for reaction for 1 hour under stirring at room temperature. After the completion of the reaction, the resultant mixture was placed and cooled in an ice-bath, adjusted by using a saturated Na₂CO₃ solution to have a pH value of 9, and subjected to reduced pressure distillation to remove methanol. The resultant aqueous phase was extracted with EtOAc. The organic phases were combined and then washed with a saturated NaCl solution, dried with anhydrous Na₂SO₄, filtered, and then concentrated to obtain a solid of 400 mg. The yield was 90%. LCMS (ESI): m/z=291 (M+H)⁺.

Step 10. (S)-2,4-diamino-6-(1-(3-chloro-5-(3-fluorophenyl)pyrazolo [1,5-a]pyrimidin-6-yl)ethylamino)pyrimidin-5-carbonitrile

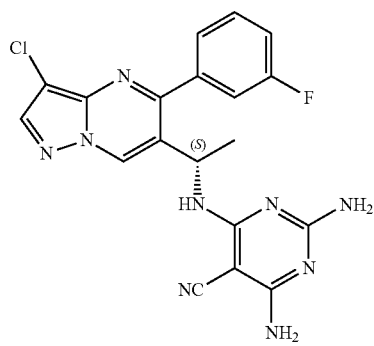

(S)-1-(3-chloro-5-(3-fluorophenyl)pyrazolo[1,5-a]pyrimidin-6-yl)ethylamine (100 mg, 0.34 mmol), 2,4-diamino-5-cyano-6-chloropyrimidine (58 mg, 0.34 mmol), KF (40 mg, 0.69 mmol), DIEA (219 mg, 1.7 mmol), and DMSO (5 mL) were added to a 25-mL round-bottom flask, and heated to 90° C. for reaction for 2 hours. After the completion of the reaction, the resultant mixture was diluted with H₂O and extracted with EtOAc. The organic phases were combined and then washed with a saturated NaCl solution, dried with anhydrous Na₂SO₄, filtered, and then concentrated to obtain a residue. The residue was purified by column chromatography (PE:EtOAc (v/v)=1:1) to obtain a solid of 70 mg. The yield was 51%. LCMS (ESI): m/z=406 (M+H)⁺. ¹H NMR (400 MHz, CDCl₃) δ 8.70 (s, 1H), 8.03 (s, 1H), 7.72-7.52 (m, 2H), 7.45-7.28 (m, 2H), 5.44-5.29 (m, 1H), 5.26-5.13 (m, 1H), 5.09 (s, 2H), 4.78 (s, 2H), 1.55 (d, J=7.0 Hz, 3H).

Example 4

(S)-4-amino-6-(1-(3-chloro-5-(3-fluorophenyl)pyrazolo[1,5-a]pyrimidin-6-yl)ethylamino)pyrimidin-5-carbonitrile

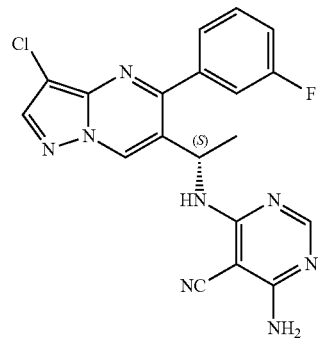

(S)-1-(3-chloro-5-(3-fluorophenyl)pyrazolo[1,5-a]pyrimidin-6-yl)ethylamine (100 mg, 0.34 mmol), 4-amino-5-cyano-6-chloropyrimidine (53 mg, 0.34 mmol), KF (40 mg, 0.69 mmol), DIEA (219 mg, 1.7 mmol), and DMSO (5 mL) were added to a 25-mL round-bottom flask, and heated to 90° C. for reaction for 2 hours. After the completion of the reaction, the resultant mixture was diluted with H₂O and extracted with EtOAc. The organic phases were combined and then washed with a saturated NaCl solution, dried with anhydrous Na₂SO₄, filtered, and then concentrated to obtain a residue. The residue was purified by column chromatography (PE:EtOAc (v/v)=1:1) to obtain a solid of 50 mg. The yield was 36%. LCMS (ESI): m/z=409 (M+H)⁺. ¹H NMR (400 MHz, CDCl₃) δ 8.67 (s, 1H), 8.10-7.98 (m, 2H), 7.68-7.54 (m, 2H), 7.42-7.28 (m, 2H), 5.54 (d, J=6.0 Hz, 1H), 5.41 (s, 2H), 5.22-5.10 (m, 1H), 1.57 (d, J=7.1 Hz, 3H).

Example 5

(S)-2-amino-4-((1-(3-chloro-5-phenylpyrazolo[1,5-a]pyrimidin-6-yl)ethyl)amino)-6-methylpyrimidin-5-carbonitrile

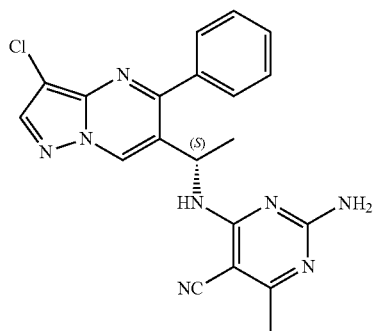

Step 1. 4-chloro-5-iodo-6-methylpyrimidin-2-amine

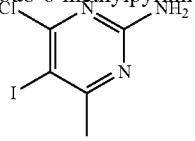

4-chloro-6-methylpyrimidin-2-amine (3 g, 21.0 mmol) was dissolved in 40 mL of glacial acetic acid in a 100-mL round-bottom flask, and then placed in an ice-bath and cooled to 10° C. below, followed by an addition of NIS (2.4 g, 10.6 mmol) to the upper solution for reaction. After the reaction proceeded for 1 hour, NIS (2.4 g, 10.6 mmol) was further added. After the reaction proceeded for 1 hour, the resultants were warmed naturally to room temperature and reacted for 8 hours. After the reaction was finished, the reactant solution was poured into ice water, and extracted with EtOAc. The resultant organic phase was washed in sequence with 5% $Na_2SO_3$ solution, 10% $NaHCO_3$ solution, and a saturated NaCl solution, dried with anhydrous $Na_2SO_4$, filtered, and then subjected to reduced pressure concentration to remove the solvent, to obtain a solid of 4.9 g, which was the captioned compound. The yield was 87%. LCMS (ESI): m/z=270 $(M+H)^+$.

Step 2. 2-amino-4-chloro-6-methylpyrimidin-5-carbonitrile

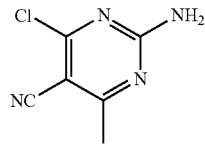

Under nitrogen atmosphere, 4-chloro-5-iodo-6-methylpyrimidin-2-amine (4.9 g, 18.2 mmol), $Zn(CN)_2$ (4.3 g, 36.6 mmol), $Pd(PPh_3)_4$ (2.1 g, 1.8 mmol), CuI (1.7 g, 8.9 mmol), and DMF (60 mL) were added to a 150-mL round-bottom flask, heated to 80° C. to react for 16 hours. After the completion of the reaction, the resultant mixture was diluted with EtOAc, and filtered through Celite to obtain a filter residue and a filtrate. The filter residue was washed with EtOAc. $H_2O$ was added to the filtrate, and the filtrate was extracted with EtOAc. The resultant organic phase was washed with a saturated NaCl solution, dried with anhydrous $Na_2SO_4$, filtered, and then concentrated to obtain a residue which was purified by column chromatography (PE:EtOAc (v/v)=5:1) to obtain a solid of 1.1 g. The yield was 36%. LCMS (ESI): m/z=169 $(M+H)^+$.

Step 3. (S)-2-amino-4-((1-(3-chloro-5-phenylpyrazolo[1,5-a]pyrimidin-6-yl) ethyl)amino)-6-methylpyrimidin-5-carbonitrile

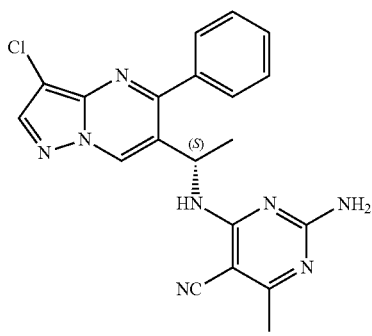

(S)-1-(3-chloro-5-phenylpyrazolo[1,5-a]pyrimidin-6-yl) ethylamine (100 mg, 0.37 mmol), 2-amino-4-chloro-6-methylpyrimidin-5-carbonitrile (62 mg, 0.37 mmol), KF (43 mg, 0.74 mmol), DIEA (232 mg, 1.8 mmol), and DMSO (5 mL) were added to a 25-mL round-bottom flask, and heated to 90° C. for reaction for 2 hours. After the completion of the reaction, the resultant mixture was diluted with $H_2O$ and extracted with EtOAc. The organic phases were combined and then washed with a saturated NaCl solution, dried with anhydrous $Na_2SO_4$, filtered, and then concentrated to obtain a residue. The residue was purified by column chromatography (PE:EtOAc (v/v)=1:1) to obtain a solid of 102 mg. The yield was 68%. LCMS (ESI): m/z=405 $(M+H)^+$. $^1H$ NMR (400 MHz, $CDCl_3$) δ 8.70 (s, 1H), 8.03 (s, 1H), 7.79-7.31 (m, 5H), 5.76 (d, J=6.7 Hz, 1H), 5.66-4.71 (m, 3H), 2.39 (s, 3H), 1.63 (d, J=7.1 Hz, 3H).

The use of the compounds of the present application for regulating the activity of a kinase and inhibiting cell proliferation is tested by the methods described below.

Example A: Activity of PI3K Kinase Assay

Activity of PI3Kδ kinase was tested by ADP-Glo method. ADP-Glo was obtained from Promega (#V9101). p110δ/p85α was obtained from Millipore (#14-604-K). The $IC_{50}$ of each of the compounds was evaluated by testing the compound at 10 concentrations. The starting concentration was 1 μM, and then a 3-fold serial dilution was performed. Buffer solutions for the testing were 50 mM HEPES pH 7.5, 3 mM $MgCl_2$, 1 mM EGTA, 100 mM NaCl, 0.03% CHAPS, and 2 mM DTT. The final concentration of the PI3Kδ kinase was 17 nM; the final concentration of PIP2 was 50 μM; and the final concentration of ATP was 25 μM.

1. Preparation of 10 μL of kinase reaction solution: 2.5 μL of test compound solution, 2.5 μL of kinase solution, and 5 μL of substrate solution were added to each well of a 384-well plate (Corning #4512).
2. The 384-well plate was covered and incubated at room temperature for 60 minutes.
3. 5 μL of reaction solution was transferred from each well to the wells of a new 384-well plate.
4. 5 μL of ADP-Glo reagent was added to the wells of the 384-well plate to terminate the reaction.
5. The 384-well plate was shaken gently on a shaking machine. 6. 10 μL of kinase detection reagent was added to each of the wells, followed by shaking for 1 minute and allowing to standing at room temperature for 30 minutes.
8. The luminescence values of the sample were read using Synegy. 9. Data were processed using Excel and was curve-fitted using XLFit software to obtain the $IC_{50}$ value of each of the compounds (Table 1).

Example B. Inhibition of Cell Activity Assay of the Compounds

CellTiter-Glo testing method was used to test the inhibition of the proliferation of lymphoma cell SU-DHL-6 (ATCC, Catalog number: CRL-2959) by the compounds. The cell culture solution used in the test was RPMI1640 (Invitrogen, Catalog number: 11875-093). 10% fetal calf serum (Invitrogen, Catalog number: 10099-141) was used in the test.

100 μL of culture solution containing 15000 cells was distributed to wells of a 96-well plate (Corning #3903). The plate was placed in a carbon dioxide incubator overnight. 0.5 μL of the compound (which was prepared using DMSO to have eight continuous concentration gradients) to be tested was added to each of the wells the next day. Each concentration was set with two replicates, and a well without cell (blank control) and a DMSO-well (solvent control). After dosing, the cells were cultured at 37° C. in 5% $CO_2$ atmosphere for 72 hours. At last, 100 μL of CellTiter-Glo agent (Promega, Catalog number: G7571) was added to each of the wells. Luminescence signal was detected using Flex Station3 (Molecular Devices), and the $IC_{50}$ value of each of the compounds inhibiting cell proliferation was calculated using XLfit software (Table 1).

TABLE 1

Activity of Kinase and Activity of Cells Inhibited by Compounds

| Compounds | PI3Kδ $IC_{50}$ (nM) | SU-DHL-6 $IC_{50}$ (nM) |
|---|---|---|
| Example 1 | A | B |
| Example 2 | A | A |
| Example 3 | A | A |
| Example 4 | A | B |
| Example 5 | A | B |

A: <20 nM;
B: 20-100 nM;
C: >100-1000 nM

As can be seen from Table 1, the compounds of the present application have excellent capability of inhibiting activity of PI3Kδ kinase. The compounds of the present application are also capable of effectively inhibiting proliferation of lymphoma cells.

The invention claimed is:

1. A compound or a pharmaceutical salt thereof, wherein the compound is selected from a group consisting of:
(S)-4-amino-6-(1-(3-chloro-5-phenylpyrazolo[1,5-a]pyrimidin-6-yl)ethylamino)pyrimidin-5-carbonitrile, (S)-2,4-diamino-6-(1-(3-chloro-5-phenylpyrazolo[1,5-a]pyrimidin-6-yl)ethylamino)pyrimidin-5-carbonitrile, (S)-2,4-diamino -6-(1-(3-chloro-5-(3-fluorophenyl)pyrazolo[1,5-a]pyrimidin-6-yl)ethylamino)pyrimidin-5-carbonitrile, (S)-4-amino-6-(1-(3-chloro-5-(3-fluorophenyl)pyrazolo[1,5-a]pyrimidin-6-yl)ethylamino) pyrimidin-5-carbonitrile, and (S)-2-amino-4-((1-(3-chloro-5-phenylpyrazolo[1,5-a]pyrimidin-6-yl)ethyl) amino)-6-methylpyrimidin-5-carbonitrile.

\* \* \* \* \*